United States Patent [19]

Pitteloud

[11] Patent Number: 5,405,891

[45] Date of Patent: Apr. 11, 1995

[54] OLIGOMERIC HALS PHOSPHITES AND HALS PHOSPHONITES AS STABILISERS

[75] Inventor: Rita Pitteloud, Praroman, Switzerland

[73] Assignee: Ciba-Geigy Corporation, Ardsley, N.Y.

[21] Appl. No.: 159,410

[22] Filed: Nov. 30, 1993

[30] Foreign Application Priority Data

Dec. 4, 1992 [CH] Switzerland .................. 3722/92

[51] Int. Cl.[6] ................ C08K 5/3435; C07F 9/06; C07C 303/00
[52] U.S. Cl. .................... 524/102; 524/103; 524/111; 252/400.24; 252/403; 546/24
[58] Field of Search ............ 252/400.24, 403; 524/102, 103, 111; 546/24

[56] References Cited

U.S. PATENT DOCUMENTS

| | | | |
|---|---|---|---|
| 4,136,083 | 1/1979 | Irick, Jr. et al. | 546/188 |
| 4,233,412 | 11/1980 | Rody et al. | 525/167 |
| 4,325,863 | 4/1982 | Hinsken et al. | 624/111 |
| 4,338,244 | 7/1982 | Hinsken et al. | 524/109 |
| 5,175,312 | 12/1992 | Dubs et al. | 549/307 |

FOREIGN PATENT DOCUMENTS

| | | |
|---|---|---|
| 356688 | 3/1990 | European Pat. Off. |
| 0511156 | 1/1993 | European Pat. Off. |
| 2335519 | 7/1977 | France |
| 3928291 | 2/1991 | Germany |
| 290906 | 6/1991 | Germany |
| 2247241 | 2/1992 | United Kingdom |

OTHER PUBLICATIONS

R. Gächter et al. Plastics Additives Handbook 3rd. Edition p. 47 (1990).
W. D. Habicher et al. J. Prakt. Chemie vol. 334, 333 (1992).
Chem. Abstracts vol. 115, 9059b.
R. A. Bartlett et al. J. Amer. Chem. Soc. vol. 109 (19), 5699 (1987).
Organic synthesis Coll. vol. IV, 784 (1963).
Thiweil et al., Helv. 1952, 1412.
F. Nief et al. Tetrahedron vol. 47 (33), 6673 (1991).

*Primary Examiner*—Kriellion S. Morgan
*Attorney, Agent, or Firm*—Luther A. R. Hall

[57] ABSTRACT

Novel oligomeric compounds of formula I

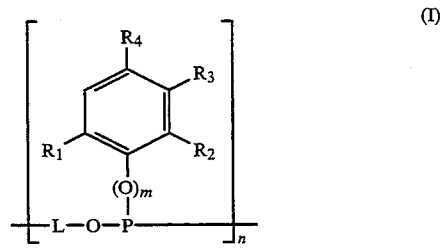

wherein L is a group of formula

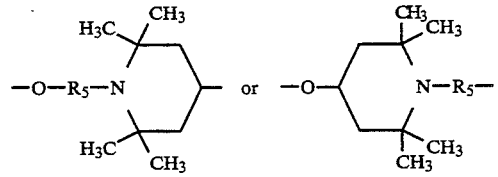

wherein the oxygen atom in the group L is attached to the phosphorus atom in the structural repeating unit, and $R_5$ or the carbon atom in 4-position of the piperidinyl ring in the group L is attached to the oxygen atom in the structural repeating unit, and the remaining symbols are as defined in claim 1, are disclosed as stabilizers for protecting organic material against oxidative, thermal or light-induced degradation.

17 Claims, No Drawings

OLIGOMERIC HALS PHOSPHITES AND HALS PHOSPHONITES AS STABILISERS

The present invention relates to novel oligomeric HALS phosphites and HALS phosphonites, to compositions comprising an organic material, preferably a polymer, and said novel oligomeric HALS phosphites and HALS phosphonites, as well as to the use thereof for stabilising organic materials against oxidative, thermal or light-induced degradation.

Organic phosphites are known in the an as co-stabilisers, secondary antioxidants and processing stabilisers, inter alia for polyolefins. Examples of such known phosphite stabilisers will be found in R. Gächter/H. Müller (Ed.), Plastics Additives Handbook, 3rd Ed., p. 47, Hanser, Munich 1990, and in EP-A-356 688.

Hindered amines, including in particular compounds containing 2,2,6,6-tetramethylpiperidyl groups, preferably find utility as light stabilisers (hindered amine light stabilisers; HALS).

Phosphites or phosphonites containing HALS structural units have been described by W. D. Habicher et al, J. prakt. Chem. 334, 333–349 (1992) and in GB-A-2 247 241.

There is still a need to provide effective stabilisers for organic materials that are susceptible to oxidative, thermal and/or light-induced degradation.

It has now been found that a selected group of such HALS phosphites and HALS phosphonites are especially suitable for use as stabilisers for organic materials that are susceptible to oxidative, thermal or light-induced degradation. The suitability of the said compounds as processing stabilisers for synthetic polymers is to be particularly highlighted.

Specifically, the invention relates to oligomeric compounds of formula I

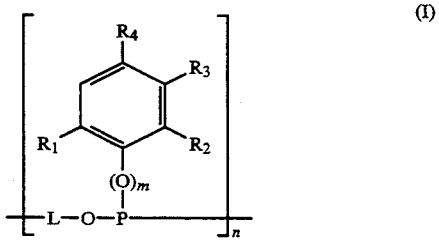

wherein L is a group of formula

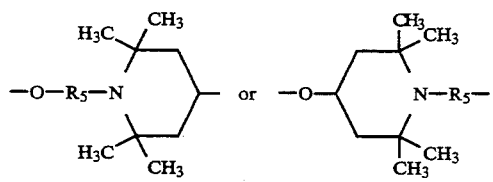

wherein the oxygen atom in the group L is attached to the phosphorus atom in the structural repeating unit, and $R_5$ or the carbon atom in 4-position of the piperidinyl ring in the group L is attached to the oxygen atom in the structural repeating unit; $R_1$ and $R_2$ are each independently of the other hydrogen, $C_1$–$C_{25}$alkyl, $C_2$–$C_{24}$alkenyl, unsubstituted or $C_1$–$C_4$alkyl-substituted $C_5$–$C_8$cycloalkyl, unsubstituted or $C_1$–$C_4$alkyl-substituted phenyl, unsubstituted or $C_1$–$C_4$alkyl-substituted $C_5$–$C_8$cycloalkenyl; $C_7$–$C_9$phenyl-alkyl or —$CH_2$—S—$R_6$, $R_3$ is hydrogen or methyl, $R_4$ is hydrogen, $C_1$–$C_{25}$alkyl, $C_2$–$C_{24}$alkenyl, unsubstituted or $C_1$–$C_4$alkyl-substituted $C_5$–$C_8$cycloalkyl, unsubstituted or $C_1$–$C_4$alkyl-substituted phenyl, unsubstituted or $C_1$–$C_4$-alkyl-substituted $C_5$–$C_8$cycloalkenyl; $C_7$–$C_9$phenylalkyl, —$CH_2$—S—$R_6$, —$(CH_2)_p COOR_7$ or —$(CH_2)_q OR_8$, $R_5$ is $C_1$–$C_{18}$alkylene, $C_2$–$C_{18}$alkylene which is interrupted by oxygen, sulfur or >N—$R_9$; or is $C_4$–$C_8$alkenylene or phenylethylene, $R_6$ is $C_1$–$C_{18}$alkyl, unsubstituted or $C_1$–$C_4$alkyl-substituted $C_5$–$C_{12}$cycloalkyl, unsubstituted or $C_1$–$C_4$alkyl-substituted phenyl; $C_7$–$C_9$phenylalkyl or —$(CH_2)_r COOR_7$, $R_7$ is $C_1$–$C_{18}$alkyl, unsubstituted or $C_1$–$C_4$alkyl-substituted $C_5$–$C_{12}$cycloalkyl, unsubstituted or $C_1$–$C_4$alkyl-substituted phenyl; or $C_7$–$C_9$phenylalkyl, $R_8$ is $C_1$–$C_{25}$alkyl, unsubstituted or $C_1$–$C_4$alkyl-substituted phenyl; $C_7$–$C_9$phenylalkyl, $C_1$–$C_{25}$alkanoyl, $C_3$–$C_{25}$alkenoyl, $C_2$–$C_{25}$alkanoyl which is interrupted by oxygen, sulfur or >N—$R_9$; $C_6$–$C_9$cycloalkylcarbonyl, unsubstituted or $C_1$–$C_{12}$alkyl-substituted benzoyl; thenoyl or furoyl, $R_9$ is hydrogen or $C_1$–$C_8$alkyl, m is 0 or 1, n is an integer from 2 to 50, p is 0, 1 or 2, q is an integer from 3 to 8, and r is 1 or 2, with the proviso that, in the structural repeating units of formula I, L, $R_1$, $R_2$, $R_3$, $R_4$, $R_5$, $R_6$, $R_7$, $R_8$ and $R_9$ as well as the indices m, p, q and r are identical or different.

Alkyl of up to 25 carbon atoms is a branched or unbranched radical and is typically methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. A preferred meaning of $R_1$, $R_2$, $R_4$ and $R_7$ is typically $C_1$–$C_{18}$alkyl. A particularly preferred meaning of $R_1$, $R_2$, $R_4$ and $R_7$ in the significance of alkyl is $C_1$–$C_4$alkyl. A particularly preferred meaning of $R_1$, $R_2$ and $R_4$ in the significance of alkyl is tert-butyl. A particularly preferred meaning of $R_7$ in the significance of alkyl is methyl.

Alkenyl 2 to 24 carbon atoms is a branched or unbranched radical such as vinyl, propenyl, 2-butenyl, 3-butenyl, isobutenyl, n-2,4-pentadienyl, 3-methyl-2-butenyl, n-2-octenyl, n-2dodecenyl, isododecenyl, oleyl, n-2-octadecenyl or n-4-octadecenyl. Preferred alkenyl is alkenyl of 3 to 18, more particularly 3 to 12, typically 3 to 6, most preferably 3 to 4, carbon atoms.

Unsubstituted or $C_1$–$C_4$alkyl-substituted $C_5$–$C_8$cycloalkyl, especially $C_5$–$C_6$cycloalkyl which preferably contains 1 to 3, more particularly 1 or 2, branched or unbranched alkyl radicals, is typically cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Cyclohexyl and tert-butylcyclohexyl are preferred.

$C_1$–$C_4$Alkyl-substituted phenyl which preferably contains 1 to 3, more particularly 1 or 2, alkyl groups, is typically o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Unsubstituted or $C_1$–$C_4$alkyl-substituted $C_5$–$C_8$cycloalkenyl which preferably contains 1 to 3, more particularly 1 or 2, branched or unbranched alkyl radicals, is typically cyclopentenyl, methylcyclopentenyl, dimethylcyclopentenyl, cyclohexenyl, methylcyclohexenyl, dimethylcyclohexenyl, trimethylcyclohexenyl, tert-butylcyclohexenyl, cycloheptenyl or cyclooctenyl. Cyclohexenyl and tert-butylcyclohexenyl are preferred.

$C_7$–$C_9$Phenylalkyl is typically benzyl, α-methylbenzyl, α,α-dimethylbenzyl or 2-phenylethyl. Benzyl is preferred.

$C_1$–$C_{18}$Alkylene is a branched or unbranched radical and is typically methylene, ethylene, propylene, tetramethylene, pentamethylene, hexamethylene, heptamethylene, octamethylene, decamethylene, dodecamethylene or octadecamethylene. $C_1$–$C_8$Alkylene is preferred. A preferred meaning of $R_5$ is ethylene and propylene.

$C_2$–$C_{18}$Alkylene which is interrupted by oxygen, sulfur or >N—$R_9$ is typically —$CH_2$—O—$CH_2$—, —$CH_2$—S—$CH_2$—, —$CH_2$—NH—$CH_2$—, —$CH_2$—N($CH_3$)—$CH_2$—, —$CH_2$—O—$CH_2CH_2$—O—$CH_2$—, —$CH_2$—(O—$CH_2CH_2$—)$_2$O—$CH_2$—, —$CH_2$—(O—$CH_2CH_2$—)$_3$O—$CH_2$—, —$CH_2$—(O—$CH_2CH_2$—)$_4$O—$CH_2$— or —$CH_2CH_2$—S—$CH_2CH_2$—.

$R_5$ in the significance of $C_4$–$C_8$alkenylene is typically 2-buten-1,4-ylene.

Unsubstituted or $C_1$–$C_4$alkyl-substituted $C_5$–$C_{12}$cycloalkyl which contains preferably 1 to 3, more particularly 1 or 2, branched or unbranched alkyl radicals, is typically cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl or cyclodecyl. Cyclohexyl and tert-butylcyclohexyl are preferred.

Alkanoyl containing up to 25 carbon atoms is a branched or unbranched radical such as formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. Alkanoyl of 2 to 18, more particularly 2 to 12, typically 2 to 6, carbon atoms, is preferred.

Alkenoyl of 3 to 25 carbon atoms is a branched or unbranched radical such as propenoyl, 2-butenoyl, 3-butenoyl, isobutenoyl, n-2,4-pentadienoyl, 3-methyl-2-butenoyl, n-2-octenoyl, n-2-dodecenoyl, isododecenoyl, oleoyl, n-2-octadecenoyl or n-4-octadecenoyl. Alkenoyl of 3 to 18, more particularly 2 to 12, typically 2 to 6, carbon atoms, is preferred.

$C_2$–$C_{25}$Alkanoyl which is interrupted by oxygen, sulfur or >N—$R_9$, preferably $C_3$–$C_{25}$alkanoyl, is typically $CH_3$OCO—, $CH_3$—O—$CH_2$CO—, $CH_3$—S—$CH_2$CO—, $CH_3$—NH—$CH_2$CO—, $CH_3$—N($CH_3$)—$CH_2$CO—, $CH_3$—O—$CH_2CH_2$—O—$CH_2$CO—, $CH_3$—(O—$CH_2CH_2$—)$_2$O—$CH_2$CO—, $CH_3$—(O—$CH_2CH_2$—)$_3$O—$CH_2$CO— or $CH_3$—(O—$CH_2CH_2$—)$_4$O—$CH_2$CO—.

$C_6$–$C_9$Cycloalkylcarbonyl is typically cyclopentylcarbonyl, cyclohexylcarbonyl, cycloheptylcarbonyl or cyclooctylcarbonyl. Cyclohexylcarbonyl is preferred.

$C_1$–$C_{12}$Alkyl-substituted benzoyl which contains preferably 1 to 3, more particularly 1 or 2, alkyl groups, is typically o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl.

Preferred oligomeric compounds of formula I are those wherein $R_1$ and $R_2$ are each independently of the other hydrogen, $C_1$–$C_{18}$alkyl, $C_2$–$C_{18}$alkenyl, $C_5$–$C_8$cycloalkyl, unsubstituted or $C_1$–$C_4$alkyl-substituted phenyl; $C_5$–$C_8$cycloalkenyl, $C_7$–$C_9$phenylalkyl or —$CH_2$—S—$R_6$, $R_4$ is hydrogen, $C_1$–$C_{18}$alkyl, $C_2$–$C_{18}$alkenyl, $C_5$–$C_8$cycloalkyl, unsubstituted or $C_1$–$C_4$-alkyl-substituted phenyl; $C_5$–$C_8$cycloalkenyl, $C_7$–$C_9$phenylalkyl, —$CH_2$—S—$R_6$, —($CH_2$)$_p$COO$R_7$ or —($CH_2$)$_q$O$R_8$, $R_5$ is $C_1$–$C_{12}$alkylene, $C_4$–$C_8$alkenylene or phenylethylene, $R_6$ is $C_1$–$C_{18}$alkyl, $C_5$–$C_{12}$cycloalkyl, unsubstituted or $C_1$–$C_4$alkyl-substituted phenyl; $C_7$–$C_9$phenylalkyl or —($CH_2$)$_r$COO$R_7$, $R_7$ is $C_1$–$C_{18}$alkyl, $C_5$–$C_{12}$cycloalkyl, unsubstituted or $C_1$–$C_4$alkyl-substituted phenyl; or $C_7$–$C_9$phenylalkyl, $R_8$ is $C_1$–$C_{18}$alkyl, unsubstituted or $C_1$–$C_4$alkyl-substituted phenyl; $C_7$–$C_9$phenylalkyl, $C_1$–$C_{18}$alkanoyl, $C_3$–$C_{18}$alkenoyl, $C_2$–$C_{18}$alkanoyl which is interrupted by oxygen, sulfur or >N—$R_9$; $C_6$–$C_9$cycloalkylcarbonyl, unsubstituted or $C_1$–$C_4$alkyl-substituted benzoyl, $R_9$ is hydrogen or $C_1$–$C_4$alkyl, and n is an integer from 2 to 40.

Also preferred are the oligomeric compounds of formula I, wherein $R_5$ is ethylene or propylene.

Further preferred oligomeric compounds of formula I are those wherein $R_1$ and $R_2$ are each independently of the other hydrogen or $C_1$–$C_4$alkyl, and $R_5$ is ethylene or propylene.

Particularly preferred oligomeric compounds of formula I are those wherein $R_1$ and $R_2$ are each independently of the other hydrogen or $C_1$–$C_{12}$alkyl, $C_2$–$C_{12}$alkenyl, cyclohexyl, phenyl or cyclohexenyl, $R_4$ is hydrogen, $C_1$–$C_{12}$alkyl, $C_2$–$C_{12}$alkenyl, cyclohexyl, phenyl, cyclohexenyl, benzyl, —$CH_2$—S—$R_6$, —($CH_2$)$_p$COO$R_7$ or —($CH_2$)$_q$O$R_8$, $R_5$ is $C_1$–$C_8$alkylene or phenylethylene, $R_6$ is $C_1$–$C_{12}$alkyl, $C_5$–$C_8$cycloalkyl, phenyl, benzyl or —($CH_2$)$_r$COO$R_7$, $R_7$ is $C_1$–$C_{12}$alkyl, $C_5$–$C_8$cycloalkyl, phenyl or benzyl, $R_8$ is $C_1$–$C_{12}$alkyl, phenyl, benzyl, $C_1$–$C_{12}$alkanoyl, $C_2$–$C_{12}$alkanoyl which is interrupted by oxygen; cyclohexylcarbonyl or benzoyl, n is an integer from 2 to 30, p is 2, q is an integer from 3 to 6, and r is 1.

Particularly interesting oligomeric compounds of formula I are those wherein $R_1$ and $R_2$ are each independently of the other hydrogen, $C_1$–$C_8$alkyl, cyclohexyl or phenyl,
$R_4$ is hydrogen, $C_1$–$C_8$alkyl, cyclohexyl or —$(CH_2)_pCOOR_7$,
$R_5$ is ethylene, propylene or phenylethylene,
$R_7$ is $C_1$–$C_{12}$alkyl or benzyl,
n is an integer from 2 to 20, and
p is 2.

Oligomeric compounds of formula I of very special interest are those wherein
$R_1$ and $R_2$ are each independently of the other hydrogen or $C_1$–$C_4$alkyl,
$R_3$ is hydrogen,
$R_4$ is hydrogen, $C_1$–$C_4$alkyl or —$(CH_2)_pCOOR_7$,
$R_5$ is ethylene or propylene,
$R_7$ is $C_1$–$C_4$alkyl,
n is an integer from 2 to 10, and
p is 2.

The novel oligomeric compounds of formula I can be prepared in per se known manner.

The preferred process typically comprises reacting a compound of formula II or a mixture of compounds of formula II with a compound of formula III or a mixture of compounds of formula III

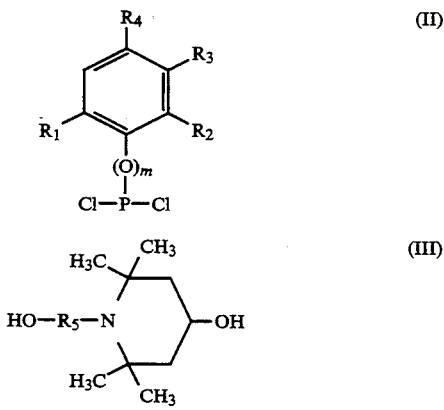

wherein $R_1$, $R_2$, $R_3$, $R_4$ and $R_5$ and the index m have the given meanings, to the oligomeric compounds of formula I.

The reaction is carried out in the melt or in the presence of a suitable organic polar or nonpolar aprotic solvent. It is preferred to carry out this reaction in the presence of a base in the temperature range from −20° C. and the boiling point of the solvent, preferably in the temperature range from 20° to 150° C.

Bases such as amines may also simultaneously be used as solvents.

Different amounts of base may be used, from catalytic through stoichiometric amounts to a multiple molar excess over the compounds of formula II or compounds of formula III. The hydrogen chloride evolved during the reaction may be converted with the base into a chloride that can be removed by filtration and/or washing with a suitable aqueous or solid phase. A second water-immiscible solvent may also be used. The products are conveniently isolated by concentrating the organic phase by evaporation and drying the residue.

Suitable solvents for carrying out the reaction typically include hydrocarbons (e.g. mesitylene, toluene, xylene, hexane, pentane or further petroleum ether fractions); halogenareal hydrocarbons (e.g. dichloro- or trichloromethane, 1,2-dichloroethane, 1,1,1-trichloroethane or chlorobenzene); ethers (e.g. diethyl ether, dibutyl ether or tetrahydrofuran), ketones (e.g. acetone, ethyl methyl ketone, diethyl ketone, methyl propyl ketone or cyclohexanone); and also acetonitrile, butyl acetate, dimethyl formamide, dimethyl sulfoxide or N-methylpyrrolidone.

Suitable bases include tertiary amines (e.g. trimethylamine, triethylamine, tributylamine, N,N-dimethylaniline, N,N-diethylaniline or pyridine), hydrides (e.g. lithium, sodium or potassium hydride) or alcoholates (e.g. sodium methanolate).

If hydrides (e.g. sodium hydride, sodium borohydrid or lithium aluminium hydride), alkali metals, alkali metal hydroxides or sodium methanolate are used as bases, then the corresponding alcoholate of the compound of formula III can be formed first. The reaction product (e.g. water, methanol) in this case is distilled off before the reaction with the compound of formula 1211 (e.g. as an azeotrope with toluene).

The structure of the oligomeric compounds of formula I is dependent on the reaction conditions, for example the solvent or the reaction temperature, as well as the molar ratio and the concentration of the compounds of formulae II and III.

The compounds of formulae I and II can be used in an equimolar ratio. It is preferred, however, to use an excess of the HALS diol of formula III. Preferred molar ratios of the compounds of formulae II to III are 1:1.05 to 1:1.9. A molar ratio of 1:1.3 to 1:1.8 is especially preferred.

The invention therefore relates also to oligomeric products obtainable by reacting a compound of formula II or of a mixture of compounds of formula II with a compound of formula III or a mixture of compounds of formula III.

The preparation of the compounds of formula III is known.

The aryl phosphorodichloridites of formula II, wherein m=1, are known or can be prepared by per se known processes, inter alia as disclosed in DE-A-3 928 291 or described by R. A. Bartlett et at, J. Amer. Chem. Soc. 109 (19), 5699 (1987).

The aryl dichlorophosphines of formula II, wherein m=0, are likewise known or can be prepared by per se known processes, as described inter alia in Org. Syntheses Coll. Vol. IV, 784 (1963) or by Th. Weil et al, Helv. Chim. Acta 1952, 1412 or F. Nief et al, Tetrahedron 47 (33), 6673 (1991).

The compounds of formula II required for the preparation of the novel compounds of formula I can be prepared in situ in analogy to the references cited above and, without isolation, further reacted with a compound of formula III to the compound of formula I.

The HALS compounds of formula III are known or can be prepared by per se known methods, as described inter alia in U.S. Pat. No. 4,233,412.

L in the structural repeating unit of formula I can have the same or different meanings.

As shown in formula IV

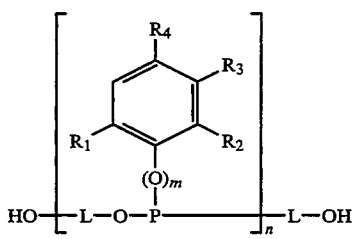

the end groups of the oligomeric compounds of formula I are mainly hydroxyl groups which can be readily derivatised by known methods. These hydroxyl groups can be esterified with acid halides, conveniently carbonyl halides or phosphoryl halides, or acid anhydrides; or alkylated or benzylated with alkyl or benzyl halides; or reacted with isocyanates to the urethanes; or derivatised with isothiocyanates to the thiourethanes; or reacted to the halides with sulfonyl halides and, conveniently, thionyl chloride; or reacted with chlorophosphites, e.g. of formula V, VI or VII

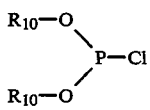

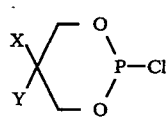

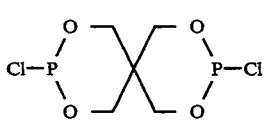

wherein $R_{10}$ is typically $C_1$–$C_{25}$alkyl, unsubstituted or $C_1$–$C_4$alkyl-substituted phenyl; or is $C_7$–$C_9$phenylalkyl, X and Y are each independently of the other hydrogen or $C_1$–$C_4$alkyl, or, together with the linking carbon atom, form a 3,4-dehydrocyclohexylidene ring.

The oligomeric compounds of formula I can also be obtained as ring systems according to formula VIII

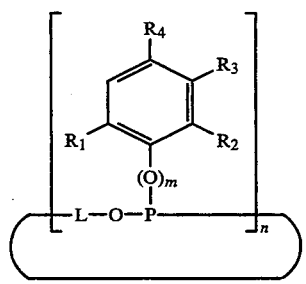

in which the hydroxy end group in L forms a ring with the other chain end

accompanied by dehydrochlorination.

The novel compounds of formula I are suitable for stabilising organic materials against oxidative, thermal or light-induced degradation.

Illustrative examples of such materials are:
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:
  a) radical polymerisation (normally under high pressure and at elevated temperature).
  b) catalytic polymerisation using a catalyst that normally contains one or more than one metal of groups IVb, Vb, VIb or VIII of the Periodic Table. These metals usually have one or more than one ligand, typically oxides, halides, alcoholams, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1 ), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from co-polyesters of saturated and unsaturated dicarboxylic acids with polyhydric alcohols and vinyl compounds as crosslinking agents, and also halogen- 24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide-/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.

The invention also relates to compositions comprising (a) an organic material that is susceptible to oxidative, thermal or light-induced degradation and (b) at least one compound of formula I.

Preferably the organic materials to be protected are natural, semi-synthetic or, more particularly, synthetic organic materials. Thermoplastic polymers are especially preferred, more particularly PVC or polyolefins, most preferably polyethylene and polypropylene.

To be particularly highlighted is the action of the novel compounds for stabilising organic materials against thermal and oxidative degradation, especially when exposed to the action of heat during the processing of thermoplastics. The novel compounds are therefore admirably suitable for use as processing stabilisers.

It is preferred to add the oligomeric compounds of formula I to the material to be stabilised in an amount of 0.01 to 10, typically 0.01 to 5, preferably 0.025 to 3 and, most preferably, 0.025 to 1% by weight. The percentages by weight are based on the weight of the organic material to be stabilised.

In addition to containing the oligomeric compounds of formula I, the novel compositions can contain further co-stabilisers, typically the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-di-phenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thio-bis(6-tert-butyl-2-methylphenol), 4,4'-thiobis(3,6-di-sec-amylphenol), 4,4'-bis-(2,6-dimethyl-4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)-pentane.

1.6. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxy-anilino)-1,3,5-triazine, 2-octylmercapto-4,6-bis(3,5-di-tert-butyl-4-hydroxyphenoxy)1,3,5-triazine, 2,4,6-tris(3,5-di-tert-butyl-4-hydroxyphenoxy)- 1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate,2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tiris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4,hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole,2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,αdimethylbenzyl)-2'-hydroxyphenyl)benzotriazole mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole 2-(3'-tert-butyl-5'-[2-(2-ethylhexyloxy)carbonyl ethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)-phenylbenzotriazole, 2,2'-methylene-bis[4-( 1,1,3,3-tetramethylbutyl)-6-benzotriazole-2-ylphenol]; the trans-esterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$]$_2^-$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives. 2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-,β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6- tetramethyl-piperidyl)succinate, bis( 1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9 9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8.2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl)4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilises, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing, agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. Nos. 4,325,863, 4,338,244 or 5,175,312, or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7 -di-tert-butyl-3-(4-ethoxyphenyl)-benzofuran-2-one, 3-(4-acetoxy-3,5-dimethylphenyl)-5,7-de-tert-butyl-benzofuran-2-one, 3-(3,5-dimethyl-4-pivaloyloxyphenyl)-5,7-di-tert-butyl-benzofuran-2-one.

The co-stabilisers, except the benzofuranones listed in item 11 ) above, are typically added in concentrations of 0.01 to 10% by weight, based on the total weight of the material to be stabilised.

Further preferred compositions contain, in addition to component (a) and the oligomeric compounds of formula I, still further additives, especially phenolic antioxidants, light stabilisers and/or processing stabilisers.

Particularly preferred additives are phenolic antioxidants (item 1 of the list), sterically hindered amines (item 2.6 of the list), phosphites and phosphonites (item 4 of the list) and peroxide scavengers (item 5 of the list).

Especially preferred additional additives (stabilisers) are the benzofuran-2-ones disclosed in, inter alia, U.S. Pat. Nos. 4,325,863, 4,338,244 or 5,175,312.

Illustrative examples of such benzofuran-2-ones are compounds of formula

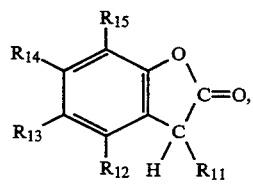

wherein
- $R_{11}$ is phenyl or phenyl which is substituted by 1 to 3 alkyl groups together containing not more than 18 carbon atoms, alkoxy of 1 to 12 carbon atoms, alkoxycarbonyl of 2 to 18 carbon atoms or chloro;
- $R_{12}$ is hydrogen;
- $R_{14}$ is hydrogen, alkyl of 1 to 12 carbon atoms, cyclopentyl, cyclohexyl or chloro;
- $R_{13}$ has the significance of $R_{12}$ or $R_{14}$ or is a radical of formula

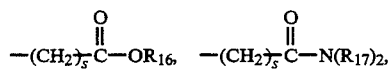

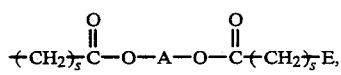

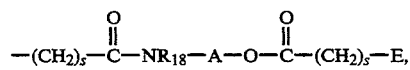

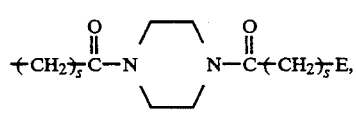

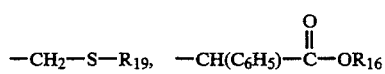

or —D—E, wherein
- $R_{16}$ is hydrogen, alkyl of 1 to 18 carbon atoms, alkyl of 2 to 18 carbon atoms which is interruped by oxygen or sulfur, dialkylaminoalkyl containing altogether 3 to 16 carbon atoms, cyclopentyl, cyclohexyl, phenyl or or phenyl which is substituted by 1 to 3 alkyl groups together containing not more than 18 carbon atoms,
- s is 0, 1 or 2;
- the $R_{17}$ substituents are each independently of the other hydrogen, alkyl of 1 to 18 carbon atoms, cyclopentyl, cyclohexyl, phenyl, phenyl which is substituted by 1 or 2 alkyl groups together containing not more than 16 carbon atoms, a radical of formula —$C_2H_4OH$,

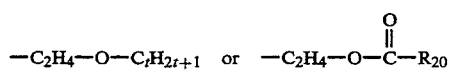

or, together with the linking nitrogen atom, form a piperidino or morpholino radical;
- t is 1 to 18;
- $R_{20}$ is hydrogen, alkyl of 1 to 22 carbon atoms or cycloalkyl of 5 to 12 carbon atoms;
- A is alkylene of 2 to 22 carbon atoms which may be interrupted by nitrogen, oxygen or sulfur;
- $R_{18}$ is hydrogen, alkyl of 1 to 18 carbon atoms, cyclopentyl, cyclohexyl, phenyl, phenyl which is substituted by 1 or 2 alkyl groups together containing not more than 16 carbon atoms, or benzyl;
- $R_{19}$ is alkyl of 1 to 18 carbon atoms;
- D is —O—, —S—, —SO—, —$SO_2$— or —$C(R_{11})_2$—;
- the $R_{21}$ substituents are each independently of the other hydrogen, alkyl of not more than 16 carbon atoms, phenyl or a radical of formula

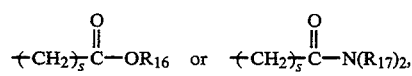

wherein s, $R_{16}$ and $R_{17}$ have the given meanings;
E is a radical of formula

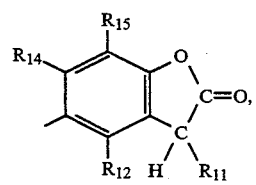

wherein $R_{11}$, $R_{12}$ and $R_{14}$ have the given meanings; and
$R_{15}$ is hydrogen, alkyl of 1 to 20 carbon atoms, cyclopentyl, cyclohexyl, chloro or a radical of formula

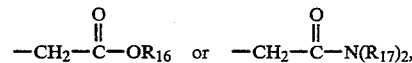

wherein $R_{16}$ and $R_{17}$ have the given meanings, or $R_{15}$ together with $R_{14}$ forms a tetramethylene radical.

Preferred benzofuran-2-ones are those in which $R_{13}$ is hydrogen, alkyl of 1 to 12 carbon atoms, cyclopentyl, cyclohexyl, chloro or a radical of formula

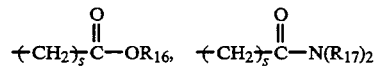

or —D—E, wherein s, $R_{16}$, $R_{17}$, D and E are as defined above, $R_{16}$ is preferably hydrogen, alkyl of 1 to 18 carbon atoms, cyclopentyl or cyclohexyl.

Further preferred benzofuran-2-ones are those in which $R_{11}$ is phenyl or phenyl which is substituted by 1 or 2 alkyl groups together containing not more than 12 carbon atoms; $R_{12}$ is hydrogen; $R_{14}$ is hydrogen or alkyl of 1 to 12 carbon atoms; $R_{13}$ is hydrogen, alkyl of 1 to 12 carbon atoms,

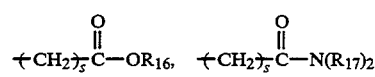

or —D—E; $R_{15}$ is hydrogen, alkyl of 1 to 20 carbon atoms,

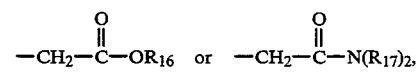

or $R_{15}$ together with $R_{14}$ forms a tetramethylene radical, in which formulae above s, $R_{16}$, $R_{17}$, D and E are as defined at the outset.

Particularly interesting benzofuran-2-ones are also those in which $R_{11}$ is phenyl; $R_{13}$ is hydrogen, alkyl of 1 to 12 carbon atoms or —D—E; $R_{12}$ and $R_{14}$ are each independently of the other hydrogen or alkyl of 1 to 4 carbon atoms; and $R_{15}$ is alkyl of 1 to 20 carbon atoms, and D and E are as defined at the outset.

Finally, those benzofuran-2-ones merit particular mention in which $R_{11}$ is phenyl; $R_{13}$ is alkyl of 1 to 4 carbon atoms or —D—E; $R_{12}$ and $R_{14}$ are hydrogen; and $R_{15}$ is alkyl of 1 to 4 carbon atoms, cyclopentyl or cyclohexyl, and D is —$C(R_{21})_2$— and E is a radical of formula

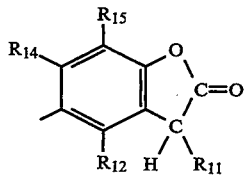

wherein the $R_{21}$ substituents are identical or different and are each alkyl of 1 to 4 carbon atoms, and $R_{11}$, $R_{12}$, $R_{14}$ and $R_{15}$ have the given meanings.

The amount of further benzofuran-2-ones, can vary over a wide range. The compositions of this invention will typically contain from 0.0001 to 5% by weight, preferably from 0.001 to 2% by weight, most preferaby from 0.01 to 2% by weight, of said additives.

The compounds of formula I and other optional additives are incorporated into the organic polymer by known methods, conveniently before or during shaping to moulded articles or alternatively by coating the organic polymers with a solution or dispersion of the compounds and subsequently evaporating the solvent. The oligomeric compounds of formula I can also be added to the materials to be stabilised in the form of a masterbatch which contains these compounds, typically in a concentration of 2.5 to 25% by weight.

The oligomeric compounds of formula I can also be added before or during polymerisation or before crosslinking.

The oligomeric compounds of formula I can be incorporated into the material to be stabilised in pure form or in waxes, oils or polymer encapsulations.

The oligomeric compounds of formula I can also be sprayed on to the polymer to be stabilised. They are able to dilute other additives (typically the conventional additives listed above) or melts thereof, so that they can also be sprayed together with these additives on to the polymer to be stabilised. Application by spraying during deactivation of the polymerisation catalysts is especially advantageous, in which case spraying is conveniently effected with the vapour used for deactivation.

It may be expedient to spray the oligomeric compounds of formula I, with or without other additives, on to spherical polymerised polyolefins.

The stabilised materials may be in any form of presentation, typically sheets, filaments, ribbons, mouldings, profiles or binders for coating compositions, adhesives or putties.

As already mentioned, the organic materials to be protected are preferably organic, more particularly synthetic, polymers. It is especially useful to protect thermoplastic polymers, preferably polyolefins. In this connection, the excellent action of the oligomeric compounds of formula I as processing stabilisers (heat stabilisers) is to be highlighted. To this end, the compounds of formula I are conveniently added before or during the processing of the polymer. It is, however, also possible to stabilise other polymers (e.g. elastomers) or lubricants and hydraulic fluids against degradation, such as light-induced and/or thermal oxidative degradation. Examples of elastomers will be found among the above list of possible organic materials.

The suitable lubricants and hydraulic fluids may be based on mineral or synthetic oils or mixtures thereof. The lubricants are known to the skilled person and described in the pertinent technical literature, for example in Dieter Klamann, "Schmierstoffe und verwandte Produkte" (Lubricants and Related Products), Verlag Chemie, Weinheim, 1982, in Schewe-Kobek, "Das Schmiermittel-Taschenbuch" (The Lubricant Handbook), Dr. Alfred Hüthig-Verlag, Heidelberg, 1974) and in "Ullmanns Enzyklopädie der technischen Chemie", (Encyclopedia of Industrial Chemistry), Vol. 13, pages 85–94 (Verlag Chemie, Weinheim, 1977).

A preferred embodiment of this invention is therefore the use of the oligomeric compounds of formula I for stabilising polymers against oxidative, thermal or light-induced degradation.

The invention further relates also to a process for stabilising an organic material against oxidative, thermal or light-induced degradation, which comprises incorporating in, or applying to, said material at least one oligomeric compound of formula I.

The invention is illustrated in more detail by the following Examples in which parts and percentages are by weight.

EXAMPLE 1

Preparation of the oligomeric compound (101) (Table 1)

a) 42.9 g (0.31 mol) of phosphorus trichloride are added dropwise to a melt kept at 50° C. of 52.9 g (0.24 tool) of 2,4-di-tert-butyl-6-methyl-phenol and 580 mg (4.8 mmol) of dimethylaminopyride. After about 1 hour the reaction mixture is heated to 100° C. and further stirred for 3 hours at this temperature. Excess phosphorus trichloride is distilled off on a rotary evaporator and the residue is distilled under a high vacuum, giving 70.0 g (91%) of 2,4-di-tert-butyl-6-methylphenylphosphorodichloridite as a colourless oil; b.p. 95° C./0.03 mbar. Analysis: calcd: C 56.09%, H 7.22%, Cl1 22.07%. Analysis: found: C 56.37%, H 7.20%, Cl1 21.97%. $^{31}$P-NMR (145.785 MHz, $CDCl_3$): 162.661 ppm.

b) A solution of 7.19 g (36 mmol; 1.7 equivalents) of N-2'-hydroxyethyl-4-hydroxy-2,2,6,6-tetramethylpiperidine in 160 ml of tetrahydrofuran is added dropwise at 10° C. to a stirred solution, under nitrogen, to 6.73 g (21.0 mmol) of 2,4-di-tert-butyl-6-methylphenylphosphorodichloridite (Example 1a) and 6.4 ml (46 mmol; 2.2 equivalents) of triethylamine in 5 ml of tetrahydrofuran. The reaction mixture is then stirred for 3 hours at a temperature of 55°–60° C. The white suspension is filtered over Celite and the filtrate is concentrated on a vacuum rotary evaporator. The residue is taken up in toluene and filtered once more. The toluene is stripped off on a vacuum rotary evaporator and the residue is dried under a high vacuum, giving 10.5 g (77%) of the oligomeric compound (101) (Table 1) of m.p. 83°–86° C.

The weight average molecular weight Mw is determined by gel permeation chromatography (GPC) and the number average molecular weight Mn is found.

The oligomeric compounds (102), (103), (104) and (105) (Table 1) are prepared from the corresponding aryl dichlorophosphites and commercially available phenyl dichlorophosphine in general accordance with the procedure described in Example 1 b.

EXAMPLE 2

Preparation of the oligomeric compound (106) (Table 1)

In general accordance with the procedure described in Example 1b, 9.3 g (98%) of the oligomeric compound (106) (Table 1), m.p. 90°–93° C., are obtained from 6.73 g (21 mmol) of 2,4-di-tert-butyl-6-methylphenylphosphorodichloridite (Example 1a) and 6.34 g (31.5 mmol; 1.5 equivalents) of N-2'-hydroxyethyl-4-hydroxy-2,2,6,6-tetramethylpiperidine.

EXAMPLE 3

Preparation of the oligomeric compound (107) (Table 1)

In general accordance with the procedure described in Example 1b, 8.6 g (91%) of the oligomeric compound (107) (Table 1), m.p. 92°–96° C., are obtained from 6.73 g (21 mmol) of 2,4-di-tert-butyl-6-methylphenylphosphorodichloridite (Example 1a) and 5.5 g (27.3 mmol; 1.3 equivalents) of N-2'-hydroxyethyl-4-hydroxy-2,2,6,6-tetramethylpiperidine.

EXAMPLE 4

Preparation of the oligomeric compound (108) (Table 1)

In general accordance with the procedure described in Example 1b, 8.5 g (90%) of the oligomeric compound (108) (Table 1), m.p. 92°–95° C., are obtained from 6.73 g (21 mmol) of 2,4-di-tert-butyl-6-methylphenylphosphorodichloridite (Example 1a) and 4.65 g (23 mmol; 1.1 equivalents) of N-2'-hydroxyethyl-4-hydroxy-2,2,6,6-tetramethylpiperidine.

EXAMPLE 5

Preparation of the oligomeric compound (109) (Table 1)

A solution of 6.73 g (21.0 mmol) of 2,4-di-tert-butyl-6-methylphenylphosphorodichloridite (Example 1a) in 10 ml of toluene is added dropwise at 10° C. to a stirred white suspension, under nitrogen, of 7.19 g (36 mmol; 1.7 equivalents) of N-2'-hydroxyethyl-4-hydroxy-2,2,6,6-tetramethylpiperidine and 5.1 g (50 mmol; 2.5 equivalents) of triethylamine in 80 ml of toluene. The reaction mixture is then vigorously stirred for 3 hours at a temperature of 95°–100° C. After cooling-to room temperature, the dense suspension is filtered over Celite and the filtrate is concentrated on a vacuum rotary evaporator. The residue is dried under a high vacuum, giving 9.5 g (75%) of the oligomeric compound (109) (Table 1) of m.p. 95°–99° C.

The oligomeric compounds (110), (111), (112) and (113) (Table 1) are prepared from the corresponding aryl dichlorophosphites and dichlorophosphines in general accordance with the procedure described in this Example.

EXAMPLE 6

Preparation of the oligomeric compound (114) (Table 1)

A solution of 9.64 g (30 mmol) of 2,4-di-tert-butyl-6-methylphenylphosphorodichloridite (Example 1a) in 10 ml of xylene is added dropwise at room temperature to a stirred suspension, under nitrogen, of 10.98 g (51 mmol; 1.7 equivalents) of N-2'-hydroxyethyl-4-hydroxy-2,2,6,6-tetramethylpiperidine and 7.59 g (75 mmol; 2.5 equivalents) of triethylamine in 170 ml of xlyene. The reaction mixture is then stirred for 5 hours at 130° C. After cooling to room temperature, the dense suspension is filtered over Celite and the filtraste is concentrated on a vacuum rotary evaporator. The residue is dried under a high vacuum, giving 16.9 g (92%) of the oligomeric compound (114) (Table 1) of m.p. 55°–72° C.

EXAMPLE 7

Preparation of the oligomeric compound (115) (Table 1)

a) 44.07 g (0.20 mol) of 2,4-di-tert-butyl-6-methylphenol, 0.49 g (4.0 mmol) of dimethylaminopyridine and 44 ml of toluene are charged, under nitrogen, to a 200 ml sulfonating flask fitted with thermometer, stirrer, reflux condenser and dropping funnel. The reaction mixture is heated to 50° C. and, at this temperature, 35.7 g (0.26 mol; 1.3 equivalents) of phosphorus trichloride are added dropwise over 20 minutes. The gaseous hydrochloric acid evolved is neutralised with a 10% aqueous solution of sodium hydroxide. The reaction mixture is thereafter heated for 95 minutes to 105° C. and further stirred for 30 minutes at this temperature (end of the evolution of gaseous hydrochloric acid). Stirring is continued for another 60 minutes at 105° C. under a gentle stream of nitrogen. The solution is diluted with 20 ml of toluene. Excess phosphorus trichloride and c. 20 ml of toluene are then removed by distillation.

b) 68.45 g (0.34 mol; 1.7 equivalents) of N-2'-hydroxyethyl-4-hydroxy-2,2,6,6-tetramethylpiperidine, 46.5 g (0.46 mol; 2.3 equivalents) of triethylamine and 1000 ml of toluene are charged, under nitrogen, to a 1.5 l sulfonating flask. The above described solution of a) is added dropwise over 45 minutes at room temperature to the resultant suspension. The dense suspension is then heated to 105° C. and further stirred for 3.5 hours at this temperature. The reaction mixture is cooled to room temperature and filtered over Celite. The filtrate is concentrated on a vacuum rotary evaporator. The residue is dried under a high vacuum, giving 82.5 g (70%) of the oligomeric compound (115) (Table 1) as a white powder of m.p. 98°–99° C.

EXAMPLE 8

Preparation of the oligomeric compound (116) (Table 1)

a) In general accordance with the procedure described in Example 7a), reaction of 33.05 g (0.15 mol) of 2,4-di-tert-butyl-6-methylphenol, 17.1 ml (0.195 mol) of phosphorus trichloride and 0.37 g (3.0 mmol) of dimethylaminopyridine in 33 ml of toluene gives the corresponding dichlorophosphite solution.

b) 71.3 g (0.255 mol) of N-2'-hydroxyethyl-4-hydroxy-2,2,6,6-tetramethylpiperidine, 170 g of triethylamine and 170 ml of toluene are charged, under nitrogen, to a 750 l sulfonating flask. The above described solution of a) is added dropwise over 45 minutes at room temperature to the resultant suspension. The dense suspension is then heated to 100° C. and further stirred for 3.5 hours at this temperature. The reaction mixture is cooled to room temperature and filtered over Celite. The filtrate is concentrated on a vacuum rotary evaporator. The residue is dried under a high vacuum, giving 75.0 g (85%) of the oligomeric compound (116) (Table 1) as a white powder of m.p. 92°–96° C.

TABLE 1

| No. | Compound | R₅ in L | Mn | Mw/Mn | m.p. (°C.) |
|---|---|---|---|---|---|
| 101 | 2,4-di-tert-butyl-6-methylphenyl phosphite polymer | —CH₂CH₂— | 1550 | 1.94 | 83–86 |
| 102 | 2,6-di-tert-butyl-4-methylphenyl phosphite polymer | —CH₂CH₂— | 1090 | 1.40 | 76–79 |
| 103 | 2,4,6-trimethylphenyl phosphite polymer | —CH₂CH₂— | 1412 | 2.3 | 58–60 |
| 104 | methyl 3-(3-tert-butyl-5-methyl-4-oxyphenyl)propanoate phosphite polymer | —CH₂CH₂— | 1699 | 2.0 | resin |
| 105 | phenylphosphonite polymer | —CH₂CH₂— | 1129 | 3.7 | 80–84 |
| 106 | 2,4-di-tert-butyl-6-methylphenyl phosphite polymer | —CH₂CH₂— | 1544 | 1.83 | 90–93 |

TABLE 1-continued
| No. | Compound | R5 in L | Mn | Mw/Mn | m.p. (°C.) |
|---|---|---|---|---|---|
| 107 | 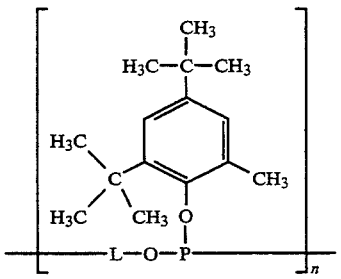 | —CH2CH2— | 2374 | 2.1 | 92–96 |
| 108 | 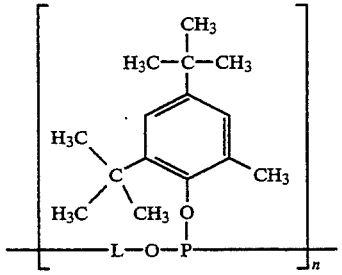 | —CH2CH2— | 2072 | 1.8 | 92–95 |
| 109 | 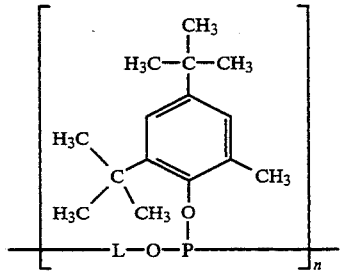 | —CH2CH2— | 2007 | 2.62 | 95–99 |
| 110 | 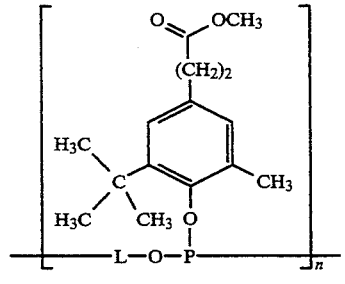 | —CH2CH2— | 2799 | 3.5 | 30 |
| 111 | 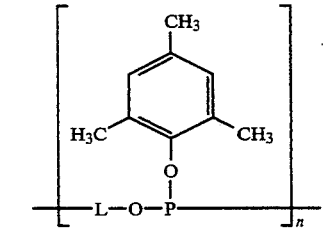 | —CH2CH2— | 2345 | 3.8 | 65–67 |
| 112 | 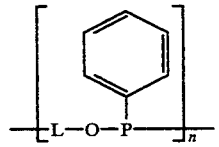 | —CH2CH2— | 2270 | 4.6 | 85–88 |

TABLE 1-continued

| No. | Compound | $R_5$ in L | Mn | Mw/Mn | m.p. (°C.) |
|-----|----------|-----------|-----|-------|-----------|
| 113 | [structure: 2,6-dimethyl-4-methylphenyl phosphite polymer] | —CH$_2$CH$_2$— | 1614 | 1.7 | 83–89 |
| 114 | [structure: 2-(1,1,3,3-tetramethylbutyl)-4-tert-butyl-6-methylphenyl phosphite polymer] | —CH$_2$CH— $\quad$ $\mid$ $\quad$ CH$_3$ | 950 | 1.7 | 55–72 |
| 115 | [structure: similar bulky phenyl phosphite polymer] | —CH$_2$CH$_2$— | 2246 | 3.31 | 98–99 |
| 116 | [structure: similar bulky phenyl phosphite polymer] | —CH$_2$CH$_2$— | 1549 | 4.61 | 92–96 |

EXAMPLE 9

Stabilisation of multiple-extruded polypropylene 1.3 kg of polypropylene powder (Profax®6501) which has been prestabilised with 0.025% of Irganox® 1076 (n-octadecyl (3-[3,5-di-tert-butyl-4-hydroxyphenyl]propionate] (having a melt index of 3.2 measured at 230°/216 kg), are blended with 0.05% of Irganox® 1010 (pentaerythrityl tetrakis-[3-(3,5-di-tert-butyl-4-hydroxyphenyl)propionate), 0.05% of calcium stearate, 0.03% of dihydrotalcite [DHT 4A ®, Kyowa Chemical Industry Co., Ltd., Mg$_{4.5}$Al$_2$(OH)$_{13}$CO$_3$.3,5-H$_2$O] and 0.05% of compound of Table 1. This blend is then extruded at 100 rpm in an extruder having a cylinder diameter of 20 mm and a length of 400 mm, the 3 heating zones being adjusted to the following temperatures: 260° C., 270° C., 280° C. The extrudate is cooled by drawing it through a water bath and then granulated. This granulate is repeatedly extruded. The melt index is measured after 3 extrusions (230° C./2.16 kg). A substantial increase in the melt index denotes pronounced chain degradation, i.e. poor stabilisation. The results are shown in Table 2.

TABLE 2

| Compound of Table 1 | Melt index after 3 extrusions |
|---------------------|-------------------------------|
| —   | 20.0 |
| 101 | 4.8  |
| 102 | 4.6  |
| 103 | 4.9  |
| 104 | 4.8  |
| 105 | 4.5  |
| 108 | 4.8  |
| 109 | 5.0  |
| 111 | 4.9  |
| 112 | 4.3  |
| 113 | 4.6  |

EXAMPLE 10

Stabilisation of multiple-extruded polypropylene 1.3 kg of polypropylene powder (Profax®6501) which has been prestabilised with 0.025% of Irganox® 1076 (n-octadecyl (3-[3,5-di-tert-butyl-4-hydroxyphenyl]propionate](having a melt index of 3.2 measured at 230°/216 kg), are blended with 0.05% of Irganox® 1010 (pentaerythrityl tetrakis-[3-(3,5-di-ten-butyl-4-hydroxyphenyl)propionate), 0.05% of calcium stearate, 0.03% of dihydrotalcite [DHT 4A ®, Kyowa Chemical Industry Co., Ltd., $Mg_{4.5}Al_2(OH)_{13}CO_3.3,5\ H_2O$] and 0.025% of compound of Table 1. This blend is then extruded at 100 rpm in an extruder having a cylinder diameter of 20 mm and a length of 400 ram, the 3 heating zones being adjusted to the following temperatures: 260° C., 270° C., 280° C. The extrudate is cooled by drawing it through a water bath and then granulated. This granulate is repeatedly extruded. The melt index is measured after 3 extrusions (230° C./2.16 kg). A substantial increase in the melt index denotes pronounced chain degradation, i.e. poor stabilisation. The results are shown in Table 3.

TABLE 3

| Compound of Table 1 | Melt index after 3 extrusions |
|---|---|
| — | 20.0 |
| 106 | 6.3 |
| 107 | 6.7 |
| 114 | 6.9 |
| 115 | 6.3 |
| 116 | 6.3 |

EXAMPLE 11

Stabilisation of polyethylene during processing 100 parts of polyethylene powder (Lupolen ® 5260 Z) are blended with 0.05 part of Irganox®1010 (pentaerythritol tetrakis[3-(3,5-di-tert-butyl-4-hydroxyphenyl)propionate]) and 0.1 part of stabiliser of Example 1 and the blend is kneaded in a Brabender plastograph at 220° C. and 50 rpm. During this time the kneading resistance is recorded continuously as torque. In the course of the kneading time the polymer begins to crosslink after prolonged constancy, as can be determined by the rapid increase in torque. The time taken until a marked increase in torque is shown in Table 4 as a measure of the stabilising action. The longer this time is the better the stabilising action.

TABLE 4

| Compound of Table 1 | Time until increase in torque (min.) |
|---|---|
| — | 5.0 |
| 101 | 12.0 |
| 103 | 12.5 |
| 105 | 14.0 |
| 107 | 14.0 |
| 109 | 12.5 |
| 111 | 12.5 |
| 115 | 14.5 |

What is claimed is:

1. An oligomeric compound of formula I

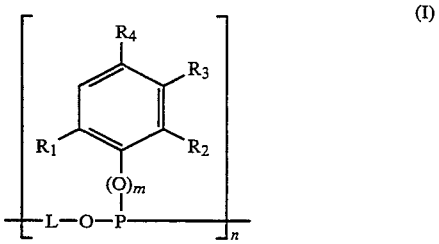

wherein L is a group of formula

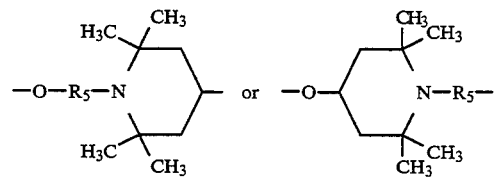

wherein the oxygen atom in the group L is attached to the phosphorus atom in the structural repeating unit, and $R_5$ or the carbon atom in 4-position of the piperidinyl ring in the group L is attached to the oxygen atom in the structural repeating unit;

$R_1$ and $R_2$ are each independently of the other hydrogen, $C_1$-$C_{25}$alkyl, $C_2$-$C_{24}$alkenyl, unsubstituted or $C_1$-$C_4$alkyl-substituted $C_5$-$C_8$cycloalkyl, unsubstituted or $C_1$-$C_4$alkyl-substituted phenyl, unsubstituted or $C_1$-$C_4$alkyl-substituted $C_5$-$C_8$cycloalkenyl; $C_7$-$C_9$phenylalkyl or —$CH_2$—S—$R_6$, $R_3$ is hydrogen or methyl, $R_4$ is hydrogen, $C_1$-$C_{25}$alkyl, $C_2$-$C_{24}$alkenyl, unsubstituted or $C_1$-$C_4$alkyl-substituted $C_5$-$C_8$cycloalkyl, unsubstituted or $C_1$-$C_4$alkyl-substituted phenyl, unsubstituted or $C_1$-$C_4$-alkyl-substituted $C_5$-$C_8$cycloalkenyl; $C_7$-$C_9$phenylalkyl, —$CH_2$—S—$R_6$, —$(CH_2)_p COOR_7$ or —$(CH_2)_q OR_8$, $R_5$ is $C_1$-$C_{18}$alkylene, $C_2$-$C_{18}$alkylene which is interrupted by oxygen, sulfur or >N—$R_9$; $C_4$-$C_8$alkenylene or phenylethylene, $R_6$ is $C_1$-$C_{18}$alkyl, unsubstituted or $C_1$-$C_4$alkyl-substituted $C_5$-$C_{12}$cycloalkyl, unsubstituted or $C_1$-$C_4$alkyl-substituted phenyl; $C_7$-$C_9$phenylalkyl or —$(CH_2)_r COOR_7$, $R_7$ is $C_1$-$C_{18}$alkyl, unsubstituted or $C_1$-$C_4$alkyl-substituted $C_5$-$C_{12}$cycloalkyl, unsubstituted or $C_1$-$C_4$alkyl-substituted phenyl; or $C_7$-$C_9$phenylalkyl, $R_8$ is $C_1$-$C_{25}$alkyl, unsubstituted or $C_1$-$C_4$alkyl-substituted phenyl; $C_7$-$C_9$phenylalkyl, $C_1$-$C_{25}$alkanoyl, $C_3$-$C_{25}$alkenoyl, $C_2$-$C_{25}$alkanoyl which is interrupted by oxygen, sulfur or >N—$R_9$; $C_6$-$C_9$cycloalkylcarbonyl, unsubstituted or $C_1$-$C_{12}$alkyl-substituted benzoyl; thenoyl or furoyl, $R_9$ is hydrogen or $C_1$-$C_8$alkyl, m is 0 or 1, n is an integer from 2 to 50, p is 0, 1 or 2, q is an integer from 3 to 8, and r is 1 or 2, with the proviso that, in the structural repeating units of formula I, L, $R_1$, $R_2$, $R_3$, $R_4$, $R_5$, $R_6$, $R_7$, $R_8$ and $R_9$ as well as the indices m, p, q and r are identical or different.

2. An oligomeric compound according to claim 1, wherein

R₁ and R₂ are each independently of the other hydrogen, $C_1$-$C_{18}$alkyl, $C_2$-$C_{18}$alkenyl, $C_5$-$C_8$cycloalkyl, unsubstituted or $C_1$-$C_4$alkyl-substituted phenyl; $C_5$-$C_8$cycloalkenyl, $C_7$-$C_9$phenylalkyl or —$CH_2$—S—$R_6$, R₄ is hydrogen, $C_1$-$C_{18}$alkyl, $C_2$-$C_{18}$alkenyl, $C_5$-$C_8$cycloalkyl, unsubstituted or $C_1$-$C_4$-alkyl-substituted phenyl; $C_5$-$C_8$cycloalkenyl, $C_7$-$C_9$Phenylalkyl, —$CH_2$—S—$R_6$, —$(CH_2)_p COOR_7$ or —$(CH_2)_q OR_8$, R₅ is $C_1$-$C_{12}$alkylene, $C_4$-$C_8$alkenylene or phenylethylene, R₆ is $C_1$-$C_{18}$alkyl, $C_5$-$C_{12}$cycloalkyl, unsubstituted or $C_1$-$C_4$alkyl-substituted phenyl; $C_7$-$C_9$phenylalkyl or —$(CH_2)_r COOR_7$, R₇ is $C_1$-$C_{18}$alkyl, $C_5$-$C_{12}$cycloalkyl, unsubstituted or $C_1$-$C_4$alkyl-substituted phenyl; or $C_7$-$C_9$phenylalkyl, R₈ is $C_1$-$C_{18}$alkyl, unsubstituted or $C_1$-$C_4$alkyl-substituted phenyl; $C_7$-$C_9$phenylalkyl, $C_1$-$C_{18}$alkanoyl, $C_3$-$C_{18}$alkanoyl which is interrupted by oxygen, sulfur or >N—$R_9$; $C_6$-$C_9$cycloalkylcarbonyl, unsubstituted or $C_1$-$C_4$alkyl-substituted benzoyl, R₉ is hydrogen or $C_1$-$C_4$alkyl, and n is an integer from 2 to 40.

3. An oligomeric compound according to claim 1, wherein R₅ is ethylene or propylene.

4. An oligomeric compound according to claim 1, wherein R₁ and R₂ are each independently of the other hydrogen or $C_1$-$C_4$alkyl, and R₅ is ethylene or propylene.

5. An oligomeric compound according to claim 1, wherein

R₁ and R₂ are each independently of the other hydrogen or $C_1$-$C_{12}$alkyl, $C_2$-$C_{12}$alkenyl, cyclohexyl, phenyl or cyclohexenyl, R₄ is hydrogen, $C_1$-$C_{12}$alkyl, $C_2$-$C_{12}$alkenyl, cyclohexyl, phenyl, cyclohexenyl, benzyl, —$CH_2$—S—$R_6$, —$(CH_2)_p COOR_7$ or —$(CH_2)_q OR_8$, R₅ is $C_1$-$C_8$alkylene or phenylethylene, R₆ is $C_1$-$C_{12}$alkyl, $C_5$-$C_8$cycloalkyl, phenyl, benzyl or —$(CH_2)_r COOR_7$, R₇ is $C_1$-$C_{12}$alkyl, $C_5$-$C_8$cycloalkyl, phenyl or benzyl, R₈ is $C_1$-$C_{12}$alkyl, phenyl, benzyl, $C_1$-$C_{12}$alkanoyl, $C_2$-$C_2$alkanoyl which is interrupted by oxygen; cyclohexylcarbonyl or benzoyl, n is an integer from 2 to 30, p is 2, q is an integer from 3 to 6, and r is 1.

6. An oligomeric compound according to claim 1, wherein

R₁ and R₂ are each independently of the other hydrogen, $C_1$-$C_8$alkyl, cyclohexyl or phenyl, R₄ is hydrogen, $C_1$-$C_8$alkyl, cyclohexyl or —$(CH_2)_p COOR_7$, R₅ is ethylene, propylene or phenylethylene, R₇ is $C_1$-$C_{12}$alkyl or benzyl, n is an integer from 2 to 20, and p is 2.

7. An oligomeric compound according to claim 1, wherein

R₁ and R₂ are each independently of the other hydrogen or $C_1$-$C_4$alkyl,

R₃ is hydrogen,

R₄ is hydrogen, $C_1$-$C_4$alkyl or —$(CH_2)_p COOR_7$,

R₅ is ethylene or propylene,

R₇ is $C_1$-$C_4$alkyl, n is an integer from 2 to 1 0, and p is 2.

8. A composition comprising a) an organic material which is susceptible to oxidative, thermal or light-induced degradation, and b) at least one oligomeric compound of formula I according to claim 1.

9. A composition according to claim 8, comprising further additives in addition to components (a) and (b).

10. A composition according to claim 9, wherein the further additives are selected from the group consisting of phenolic antioxidants, light stabilisers and processing stabilisers.

11. A composition according to claim 9, comprising at least one compound of the benzo-furan-2-one type as further additive.

12. A composition according to claim 8, wherein component (a) is a natural, semi-synthetic or synthetic polymer.

13. A composition according to claim 8, wherein component (a) is a thermoplastic polymer.

14. A composition according to claim 8, wherein component (a) is a polyolefin.

15. A composition according to claim 8, wherein component (a) is polyethylene or polypropylene.

16. A method of stabilising organic material against oxidative, thermal or light-induced degradation, which comprises incorporating in, or applying to, said material at least one oligomeric compound of formula I as defined in claim 1.

17. An oligomeric product obtainable by reacting a compound of formula II or a mixture of compounds of formula II with a compound of formula HI or a mixture of compounds of formula III

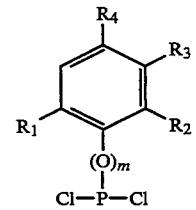
(II)

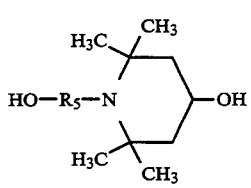
(III)

wherein R₁, R₂, R₃, R₄ and R₅ and the index m are as defined in claim 1.

* * * * *